United States Patent [19]  [11] 3,998,915
Seng  [45] Dec. 21, 1976

[54] PROCESS FOR THE PRODUCTION OF 1-ACYLOXY ALKYLENE PHOSPHONIC ACID DIALKYL ESTERS

[75] Inventor: Florin Seng, Schildgen, Germany

[73] Assignee: Bayer Aktiengesellschaft, Leverkusen, Germany

[22] Filed: June 9, 1975

[21] Appl. No.: 585,262

[30] Foreign Application Priority Data
June 29, 1974  Germany ............................ 2431408

[52] U.S. Cl. .................................. 260/971; 260/952
[51] Int. Cl.[2] ............................................ C07F 9/40
[58] Field of Search ............................ 260/971, 952

[56] References Cited
UNITED STATES PATENTS
3,836,609  9/1974  Golborn ............................. 260/971

Primary Examiner—Richard L. Raymond
Attorney, Agent, or Firm—Burgess, Dinklage & Sprung

[57] ABSTRACT

New process for producing 1-acyloxy alkylene phosphonic acid dialkyl esters comprising reacting α-oxo-alkane phosphonic acid dialkyl esters with carboxylic acid anhydrides in the presence of basic catalysts.

6 Claims, No Drawings

PROCESS FOR THE PRODUCTION OF 1-ACYLOXY ALKYLENE PHOSPHONIC ACID DIALKYL ESTERS

This invention relates to a new process for producing 1-acyloxy alkylene phosphonic acid dialkyl esters.

It is already known that 1-acyloxy ethylene phosphonic acid dialkyl esters can be obtained by reacting a dialkyl phosphite with ketene in the presence of a catalyst (J. Kennedy and G. M. Meaburn, Chem. and Ind. 1956, 930; R. L. Mc Connell and H. W. Coover Jr. J. Org. Chem 23, 830 (1958); V. J. Nikitina and A. N. Pudovik, Z. obsc. Chim. 29, 1219 (1959)). In these processes, the reaction times are relatively long and the yields obtained are only about 60%.

It has now been found that 1-acyloxy alkylene phosphonic acid dialkyl esters corresponding to the general formula (I)

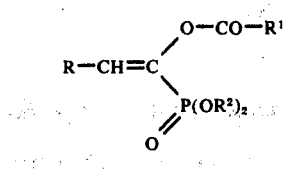

in which R represents hydrogen or a saturated aliphatic radical and $R^1$ and $R^2$ are the same or different and each represent a saturated aliphatic radical, can be obtained by a process which is characterised by the fact that α-oxoalkane phosphonic acid dialkyl esters corresponding to the general formula (II)

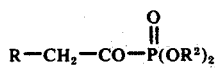

in which R and $R^2$ are as defined above, are reacted with carboxylic acid anhydrides in the presence of basic catalysts.

In general, the reaction is carried out at a temperature in the range from about 0° to about 150° C, preferably at temperatures in the range from about 20° to about 120° C and more especially at temperatures in the range from 60° to 100° C.

$R^1$ and $R^2$ may be for example linear, branched and/or cyclic saturated alkyl radicals having 1 to 18 carbon atoms, preferably having 1 to 12 carbon atoms and more especially with 1 to 6 carbon atoms. Unless it represents hydrogen, R can have the same meaning as $R^1$ and $R^2$.

α-Oxo-alkane phosphonic acid dialkyl esters of general formula II, which may be used as starting compounds in the process according to the invention, are already known or may by obtained by known methods (M. J. Kabachnik and P. A. Rossijskaja, Izv. Akad. S.S.S.R. 1945, 364; E. A. Arbusov and M. M. Azanovskaja, Doklady Adad. S.S.S.R. 58, 1961 (1947); J. A. Cade, Soc. 1959, 2272), e.g., by reacting trialkyl phosphites with carboxylic acid chlorides.

Carboxylic acid anhydrides suitable for use in the process according to the invention correspond for example to the formula

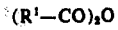

in which $R^1$ is as just defined.

Preferred basic catalysts are tertiary amines, for example pyridine, α-, β- and γ- picoline and quinoline. The quantity in which the catalyst is used may be varied within wide limits. It has proved to be advantageous to use the catalyst in a quantity of at least 0.1 mol per mol of compound of formula (II). The catalyst may be used for example in a quantity of 0.1 to 10 mols per mol of compound of formula (II). In general, the catalyst is used in at least 0.1 times the molar quantity. The catalyst may be used for example in 0.1 to 10 times the molar quantity.

In general, the process according to the invention is carried out in the absence of a solvent. However, it is possible to carry out the reaction in the presence of an inert solvent, for example a chlorinated aromatic solvent. It is also possible to use one of the reactants in excess, in which case the excess serves as solvent. In this case, it is preferably the carboxylic acid anhydride which is used in excess. In another embodiment of the process according to the invention, an excess of catalyst, for example an excess of tertiary amine, is used, the excess serving as solvent. These embodiments may also be used in combination with one another, for example adding an inert solvent and adding an excess of one of the reactants or adding one of the reactants and the catalyst in excess.

The process according to the invention may be carried out for example as follows: α-oxo-alkane phosphonic acid dialkyl ester is mixed with at least the stoichiometric quantity of an acid anhydride and heated for a few hours in the presence of a tertiary amine. The end of the reaction can be determined by infrared spectroscopy from the disappearance of the carbonyl band of the α-oxo-alkane phosphonic acid dialkyl ester used at 1700 cm$^{-1}$. The 1-acyloxyl alkylene phosphonic acid dialkyl ester may then be isolated by fractional distillation.

The reaction according to the invention is illustrated by the following equation which relates by way of example to the reaction of acetyl phosphonic acid diethyl ester and acetic acid anhydride with pyridine as basic catalyst to form 1-acetyloxy ethylene phosphonic acid diethyl ester:

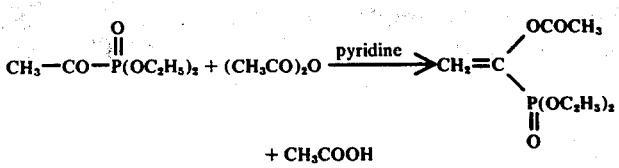

It must be regarded as extremely surprising that 1-acyloxy alkylene phosphonic acid dialkyl esters can be obtained by the process according to the invention because it had been expected from the prior art that α-oxo-alkane phosphonic acid dialkyl esters would react with carboxylic acid anhydrides to form O-acyl-1-oxo-alkane phosphonic acid esters (G. Kamai and V. A. Kuchtin, Z. obsc. Chim 27).

The advantages of the process according to the invention are the high yields which can be obtained, the relatively short reaction times and the ready workability of the process.

1-Acyloxy ethylene phosphonic acid dialkyl esters are important comonomers for the production of substantially non-inflammable polymers (U.S. Pat. No. 2,940,961 (1957) Eastman Kodak Co., inventors H. W. Coover Jr. and R. L. McConnall).

EXAMPLE 1

1-Acetyloxy ethylene phosphonic acid diethyl ester

A mixture of 36 g (0.2 mol) of 1-oxo-ethane phosphonic acid diethyl ester, 51 g (0.5 mol) of acetic acid anhydride and 18.5 g (0.2 mol) of pyridine was stirred for 3.5 hours at 60° C. The reaction mixture was then subjected to fractional distillation. After the excess acetic acid anhydride, the pyridine and the acetic acid formed had been distilled off, 1-acetyloxy ethylene phosphonic acid diethyl ester of bp: 89°–91°C/0.3 mm Hg was obtained in a yield of 42 g or 95 % of the theoretical yield.

EXAMPLE 2

A mixture of 36 g (0.2 mol) of 1-oxo ethane phosphonic acid diethyl ester, 22.4 g (0.22 mol) of acetic acid anhydride and 0.5 ml of pyridine was heated for 5 hours to 100° C. Working up in the same way as described in Example 1 gave 32 g (74% of the theoretical yield) of 1-acetyloxy ethylene phosphonic acid diethyl ester of bp 89°–91° C/0.3 mm Hg.

EXAMPLE 3

1-Propionyloxy ethylene phosphonic acid diethyl ester

A mixture of 36 g (0.2 mol) of 1-oxo ethane phosphonic acid diethyl ester, 130 g (1 mol) of propionic acid anhydride and 30 ml of pyridine was heated for 6 hours at 60° C. The reaction mixture was then subjected to fractional distillation, yielding 39 g (83% of the theoretical yield) of 1-propionyloxy ethylene phosphonic acid diethyl ester of bp: 79°–81° C/0.1 mm Hg.

EXAMPLE 4

1-Acetyloxy propylene phosphonic acid diethyl ester

A mixture of 35 g (0.18 mol) of 1-oxo propane phosphonic acid diethyl ester, 46 g (0.4 mol) of acetic acid anhydride and 30 ml of pyridine was stirred for 6 hours at 60° C. Subsequent fractional distillation gave 36 g (77% of the theoretical yield) of 1-acetyloxy propylene phosphonic acid diethyl ester of bp: 105° – 107° C/0.15 mm Hg.

EXAMPLE 5

1-Propionyloxy propylene phosphonic acid diethyl ester

A mixture of 35 g (0.18 mol) of 1-oxo propane phosphonic acid diethyl ester, 59 g (0.45 mol) of propionic acid anhydride and 30 ml of pyridine was stirred for 6 hours at 60° C. Subsequent fractional distillation gave 36 g (72% of the theoretical yield) of 1-propionyloxy propylene phosphonic acid diethyl ester of bp 110° – 113° C/0.15 mm Hg.

What we claim is:
1. In the process for the production of a 1-acyloxy alkylene phosphonic acid dialkyl ester corresponding to the general formula (I)

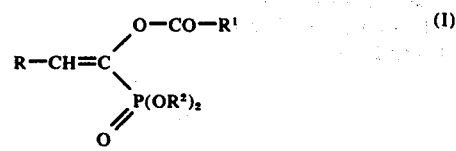

in which R represents hydrogen or a saturated aliphatic radical, and
$R^1$ and $R^2$ are the same or different and each represents a saturated aliphatic radical,
comprising reacting an α-oxo-alkane phosphonic acid dialkyl ester corresponding to the general formula (II)

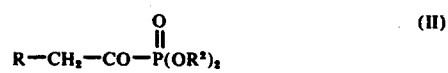

in which R and $R^2$ are as just defined,
with a carboxylic acid anhydride in the presence of a basic catalyst, and recovering the resulting 1-acyloxy alkylene phosphonic acid dialkyl ester of formula (I), the improvement comprising using as basic catalyst pyridine.

2. Process according to claim 1, wherein the reaction is carried out at a temperature in the range of from 0° to 150° C.

3. Process according to claim 1, wherein the reaction is carried out at a temperature of from 60° to 100° C.

4. Process according to claim 1, wherein the catalyst is used in a quantity of at least 0.1 mol per mole of the compound of general formula (II).

5. Process according to claim 1, wherein the catalyst is used in a quantity of from 0.1 to 10 mols per mole of the compound of general formula (II).

6. Process according to claim 1, wherein the carboxylic acid anhydride is used in excess.

* * * * *